United States Patent [19]

Mencke et al.

[11] 4,454,129

[45] Jun. 12, 1984

[54] CEPHEM DERIVATIVES

[75] Inventors: Burkhard Mencke, Idstein; Eberhard Ehlers, Hofheim am Taunus; Jürgen Blumbach, Frankfurt am Main; Walter Dürckheimer, Hattersheim am Main; Karl Seeger, Hofheim am Taunus, all of Fed. Rep. of Germany

[73] Assignee: Hoechst Aktiengesellschaft, Frankfurt am Main, Fed. Rep. of Germany

[21] Appl. No.: 373,790

[22] Filed: Apr. 30, 1982

[30] Foreign Application Priority Data

May 2, 1981 [DE] Fed. Rep. of Germany ....... 3117438

[51] Int. Cl.³ .................. A61K 31/545; C07D 501/56
[52] U.S. Cl. ..................................... 424/246; 544/27; 548/187
[58] Field of Search ........................... 424/246; 544/27

[56] References Cited

U.S. PATENT DOCUMENTS 4,098,888 7/1978 Ochiai et al. ......................... 544/27
4,278,793 7/1981 Durckheimer et al. ............... 544/27

Primary Examiner—Paul M. Coughlan, Jr.
Attorney, Agent, or Firm—Curtis, Morris & Safford

[57] ABSTRACT

What are disclosed are cephem compounds of the formula

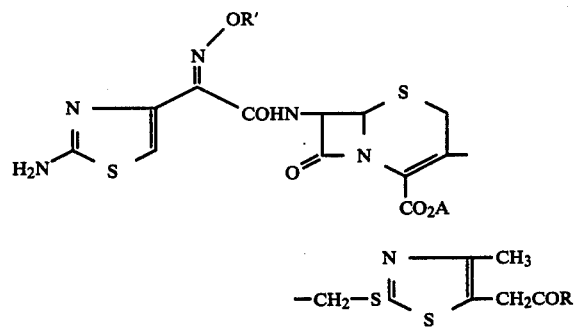

useful for combating bacterial infections, and methods of making and using the same.

8 Claims, No Drawings

CEPHEM DERIVATIVES

The invention relates to cephem derivatives of the formula I

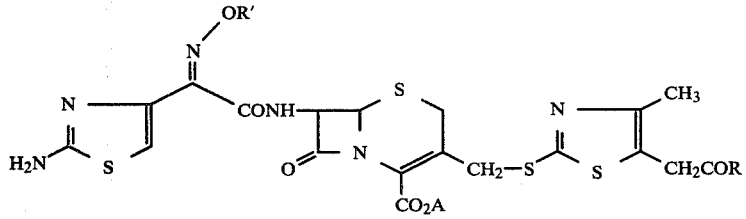

in which R denotes optionally substituted alkoxy, optionally substituted alkenoxy, alkinoxy or cycloalkoxy, optionally substituted aryloxy or optionally substituted aralkoxy, amino, alkylamino or dialkylamino in which the two alkyl groups can also be linked to form a 4- membered to 7-membered ring which can optionally also contain a further nitrogen atom or an oxygen atom, or denotes alkenylamino or optionally substituted arylamino, and R' represents hydrogen, optionally substituted alkyl, carboxymethyl in which the carboxyl group can also be present in the form of a physiologically acceptable salt or physiologically acceptable ester, alkoxycarbonylmethyl, aminocarbonylmethyl or cyanomethyl, it being possible for the methylene group in these radicals, if appropriate, to be substituted, and in which A represents hydrogen, a physiologically acceptable cation or a physiologically acceptable ester group, and in which the R'O group is in the syn-position.

The present invention thus relates to compounds of the formula I in which the substituents can, for example, have the following meaning.

R can represent alkoxy which has 1 to 6, preferably 1 to 4, C atoms and which can optionally be substituted by hydroxyl, halogen, preferably chlorine and bromine, carboxyl, aminocarbonyl, alkoxy having 1 to 4 C atoms, alkoxyalkoxy having 1 to 4 C atoms per alkyl part, alkoxyalkoxyalkoxy having 1 to 4 C atoms per alkyl part, or aryl or aryloxy, in particular phenyl or phenoxy, it being possible for aryl to be optionally monosubstituted or polysubstituted further by hydroxyl, alkyl having 1 to 4 C atoms, alkoxy having 1 to 4 C atoms, halogen, in particular chlorine and bromine, carboxyl, alkoxycarbonyl having 1 to 4 C atoms in the alkyl part, or aminocarbonyl, or can represent alkenoxy which has 2 to 6, preferably 2 to 3, C atoms and which can optionally be substituted by phenyl which can, in turn, optionally be monosubstituted or polysubstituted further by hydroxyl, alkyl having 1 to 4 C atoms, alkoxy having 1 to 4 C atoms, halogen, preferably chlorine and bromine, carboxyl, alkoxycarbonyl having 1 to 4 C atoms in the alkyl part or aminocarbonyl, or can represent alkinoxy having 2 to 6, preferably 2 to 3, C atoms, or can represent cycloalkoxy having 3 to 6, preferably 5 to 6, C atoms, or can represent aryloxy, preferably phenoxy, which can optionally be monosubstituted or polysubstituted further by halogen, in particular chlorine and bromine, alkyl having 1 to 4 C atoms, hydroxyl, alkoxy having 1 to 4 C atoms, nitro, amino, alkylamino having 1 to 4 C atoms, dialkylamino having 1 to 4 C atoms per alkyl part, sulfo, aminocarbonyl, carboxyl or alkoxycarbonyl having 1 to 4 C atoms in the alkyl part, or can represent aralkoxy, preferably phenylalkoxy, having 1 to 6, preferably 1 to 2, C atoms in the alkyl part, it being possible for the aryl part to be optionally monosubstituted or polysubstituted further by halogen, preferably chlorine and bromine, alkyl having 1 to 4 C atoms, hydroxyl, alkoxy having 1 to 4 C atoms, nitro, amino, alkylamino having 1 to 4 C atoms, dialkylamino having 1 to 4 C atoms per alkyl part, sulfo, carboxyl, alkoxycarbonyl having 1 to 4 C atoms in the alkyl part, or aminocarbonyl, or can represent amino, alkylamino having 1 to 4 C atoms in the alkyl part, or dialkylamino which has 1 to 4 C atoms per alkyl part and in which the alkyl parts can also be linked to form a 4-membered to 7-membered, preferably 5-membered to 6-membered, ring which can optionally also contain a further nitrogen atom or an oxygen atom, or can represent alkenylamino having 2 to 4, preferably 2 to 3, C atoms in the alkenyl part, or can represent arylamino, in particular phenylamino, in which the aryl part can optionally be monosubstituted or polysubstituted further by halogen, in particular chlorine or bromine, alkyl having 1 to 4 C atoms, hydroxyl, alkoxy having 1 to 4 C atoms, nitro, amino, alkylamino having 1 to 4 C atoms, dialkylamino having 1 to 4 C atoms per alkyl part, sulfo, carboxyl, alkoxycarbonyl having 1 to 4 C atoms in the alkyl part, or aminocarbonyl.

If R' represents optionally substituted alkyl, this is particularly suitably alkyl having 1 to 4 C atoms, and if R' represents optionally substituted alkoxycarbonylmethyl, here too a group containing 1 to 4 C atoms in the alkyl part is preferred.

A few groups which, in accordance with the invention, are of particular interest for the substituents R, R' and A, are listed below.

If R represents optionally substituted alkoxy having 1 to 6 C atoms, special mention should be made of methoxy, ethoxy, propoxy, isopropoxy, butoxy, isobutoxy, tert.-butoxy, methoxyethoxy, ethoxyethoxy, methoxyethoxyethoxy, methoxyethoxyethoxyethoxy, ethoxyethoxyethoxyethoxy, phenoxyethoxy, 4-chlorophenoxyethoxy, 4-methylphenoxyethoxy and 4-methoxyphenoxyethoxy, and of these, methoxy, ethoxy, isopropoxy, isobutoxy, tert.-butoxy, methoxyethoxy, methoxyethoxyethoxy, phenoxyethoxy and 4-chlorophenoxyethoxy are particularly preferred.

If R represents optionally substituted alkenoxy, allyloxy and cinnamyloxy should be mentioned as being particularly preferred.

When R denotes alkinoxy, propargyloxy is particularly preferred.

When R denotes cycloalkoxy, this can be, for example, cyclopropoxy, cyclobutoxy, cyclopentyloxy or cyclohexyloxy, but particularly cyclopentyloxy and cyclohexyloxy.

If R represents aryloxy, special mention should be made of phenoxy, 4-tolyloxy, 2-chlorophenoxy, 4-chlorophenoxy, 3,4-dichlorophenoxy, 2-hydroxyphenoxy, 4-hydroxyphenoxy, 3,4-dihydroxyphenoxy, 4-methoxyphenoxy, 3,4-dimethoxyphenoxy, 4-nitrophenoxy, 2-nitrophenoxy, 4-aminophenoxy, 4-dimethylaminophenoxy, 4-diethylaminophenoxy, 4-sulfophenoxy, 4-carboxyphenoxy, 2-carboxyphenoxy, 4-ethoxycarbonylphenoxy or 4-aminocabonylphenoxy, and of these, phenoxy, 4-chlorophenoxy, 3,4-dichlorophenoxy, 4-methoxyphenoxy, 3,4-dimethoxyphenoxy and 4-dimethylaminophenoxy are particularly preferred.

When R denotes aryl, the data applying to the substituents and preferred radicals are the same as those given for aryloxy in the preceding paragraph.

When R denotes aralkoxy, it can, for example, represent benzyloxy, 4-methylbenzyloxy, 4-chlorobenzyloxy, 4-methoxybenzyloxy, 3,4-dimethoxybenzyloxy, 4-hydroxybenzyloxy, 4-nitrobenzyloxy, 4-carboxybenzyloxy, 2-carboxybenzyloxy, 4-ethoxycarbonyloxy, 4-aminocarbonylbenzyloxy, 4-dimethylaminobenzyloxy and phenethoxy, but preferably represents benzyloxy, 4-chlorobenzyloxy, 3,4-dichlorobenzyloxy, 4-methoxybenzyloxy, 3,4-dimethoxybenzyloxy, 4-carboxybenzyloxy, 4-aminobenzyloxy and 4-dimethylaminobenzyloxy.

When R denotes alkylamino, it can, for example, represent methylamino, ethylamino, propylamino or butylamino, but preferably represents methylamino and ethylamino.

If R represents dialkylamino, the following may be mentioned as examples: dimethylamino, diethylamino, dipropylamino, diisopropylamino, 1-piperidyl, 1-pyrrolidinyl, 1-piperazinyl, 4-ethylpiperazin-1-yl or morpholin-4-yl, but dimethylamino, diethylamino, 1-piperidyl, 1-pyrrolidinyl and morpholin-4-yl are preferred.

If R represents alkenylamino, allylamino should be mentioned particularly.

When R denotes arylamino, it can, for example, represent anilino, 4-tolylamino, 4-chlorophenylamino, 4-hydroxyphenylamino, 4-methoxyphenylamino, 2-methoxyphenylamino, 4-nitrophenylamino, 4-aminophenylamino, 4-methylaminophenylamino, 4-dimethylaminophenylamino, 4-sulfophenylamino, 4-carboxyphenylamino, 2-carboxyphenylamino, 4-ethoxycarbonylphenylamino and 4-aminocarbonylphenylamino, but preferably represents anilino, 4-chlorophenylamino, 4-methoxyphenylamino, 4-carboxyphenylamino and 4-aminocarbonylamino.

If R' represents optionally substituted alkyl, substituents which are particularly suitable are halogen, preferably chlorine and bromine, hydroxyl or sulfo. Methyl, ethyl, n-propyl, isopropyl, n-butyl and isobutyl are preferred, but methyl is particularly preferred. 2-Chloroethyl and 2-bromoethyl may be mentioned as examples of preferred substituted alkyl radicals.

If R' represents alkoxycarbonylmethyl, methoxycarbonylmethyl and ethoxycarbonylmethyl are particularly suitable.

When R' denotes carboxymethyl which can also be present in the form of its physiologically acceptable salts and esters, alkoxycarbonylmethyl, aminocarbonylmethyl and cyanomethyl, the methylene group can contain one or two further substituents, for example alkyl having 1 to 4 C atoms, preferably methyl, and 2 alkyl substituents can, in particular, also be linked to form a 3-membered to 6-membered, preferably 5-membered to 6-membered, carbocyclic ring. Groups which may be mentioned as preferred for these definitions are carboxymethyl, 1-carboxyethyl, 2-carboxyethyl, 2-carboxyisopropyl, methoxycarbonylmethyl, ethoxycarbonylmethyl, aminocarbonylmethyl and cyanomethyl.

Compounds in which R' represents hydrogen are also to be regarded as preferred.

If A represents a radical which has the character of a protective group, the following may be mentioned as preferred examples: tert.-butyl and trimethylsilyl and also benzyl, benzhydryl, trichloroethyl-4-methoxybenzyl or 4-nitrobenzyl.

If A represents a physiologically acceptable ester group, a suitable example is 1-acyloxyalkyl having 1 to 6, preferably 1 to 4, C atoms in both the acyl part and the alkyl part, such as, for example, acetoxymethyl, 1-acetoxyethyl, 1-acetoxypropyl, 1-acetoxyisopropyl, 1-acetoxyhexyl, propionyloxymethyl, 1-propionyloxyethyl, 1-propionyloxypropyl, 1-propionyloxyhexyl, 1-pivaloyloxymethyl and 1-pivaloyloxyethyl, but particularly acetoxymethyl, 1-acetoxyethyl, 1-propionyloxyethyl and pivaloyloxymethyl.

The following may be mentioned as examples of physiologically acceptble cations: alkali metal ions, in particular the sodium and potassium ions, alkaline earth metal ions, in particular the calcium and magnesium ions, and an ammonium ion, but preferably a sodium ion, and also an alkylated ammonium ion which is optionally substituted and in which an alkyl radical can have 1 to 4 C atoms, such as, in particular, triethylammonium, diethylammonium, dimethylammonium or morpholinium.

Corresponding physiologically acceptable cations and esters are also suitable in the event that R' is present in the form of a salt or ester of the carboxymethyl group.

The invention also relates to a process for the preparation of cephem compounds of the formula I, which comprises reacting lactams of the formula II

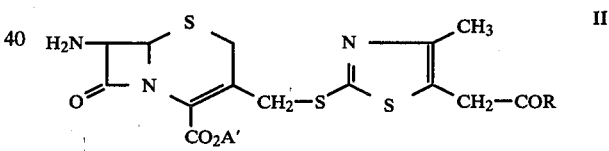

in which R has the meaning indicated above and A' represents a cation, a protective group or a physiologically acceptable ester, with a carboxylic acid of the formula III

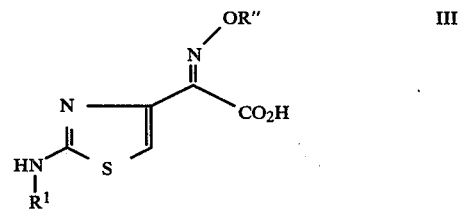

or with a reactive derivative thereof, in which $R^1$ represents hydrogen or an amino protective group which is known in peptide chemistry, and R" has the same meaning as R' or represents a protective group or a group

—$CH_2COOR^3$ which is optionally substituted on the methylene radical and in which $R^3$ can have the meaning of a protective group or of a physiologically acceptable ester, to give a compound of the formula IV

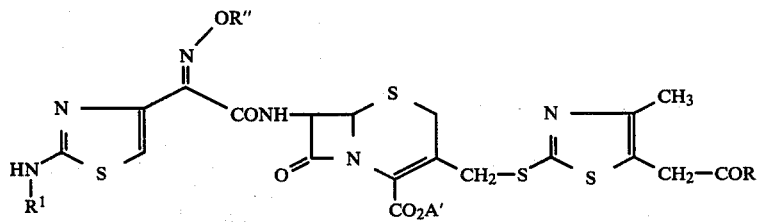

IV in which $R^1$, $R''$, R and $A'$ have the abovementioned meanings, or reacting cephem compounds of the formula VI

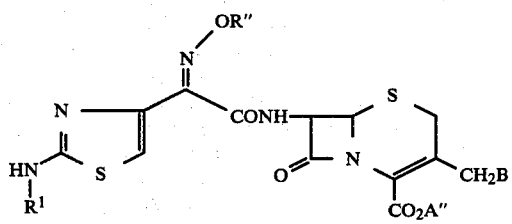

VI in which $R^1$ and $R''$ have the abovementioned meaning, $A''$ represents hydrogen or a cation and B represents a group which can be replaced by the nucleophilic radical of the compound of the formula V, with a compound of the formula V

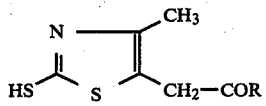

V in which R has the abovementioned meaning, and, in the resulting compounds, if desired ($\alpha$) splitting off a radical $R^1$, $R''$, $A''$ and/or $R^3$ which denotes a protective group, and ($\beta$) converting a resulting salt without further treatment or via the free carboxylic acids into a physiologically acceptable ester.

In the above formulae, $R^1$ represents hydrogen or an amino protective group which is known in peptide chemistry, such as, for example, alkyl which is optionally substituted and has 1 to 6 C atoms, such as, for example, preferably tert.-butyl, tert.-amyl, benzyl, 4-methoxybenzyl, benzhydryl, trityl and phenylethyl, aliphatic acyl which is optionally substituted and has 1 to 4 C atoms, such as, for example, preferably formyl, chloroacetyl, bromoacetyl, trichloroacetyl and trifluoroacetyl, or alkoxycarbonyl which is optionally substituted and has 1 to 4 C atoms in the alkyl part, such as, for example, trichloroethoxycarbonyl or benzyloxycarbonyl, $R''$, insofar as it has the function of a protective group, represents, for example, formyl, trifluoroacetyl, chloroacetyl, bromoacetyl, trityl, tert.-amyl, tert.-butyl, benzhydryl and tetrahydropyranyl, but preferably represents tert.-butyl, trityl and tetrahydropyranyl, and also represents a group of the formula —$CH_2COOR^3$ in which the methylene group can optionally be substituted and in which $R^3$ denotes a protective group, such as, for example, preferably trichloroethyl, tert.-butyl, benzyl, 4-methoxyphenyl, benzhydryl or trityl, and $R^3$ can also represent a physiologically acceptable ester radical, $A'$ represents a cation, a protective group or a physiologically acceptable ester group such as those already described as examples under A, $A''$ represents hydrogen or a cation, for example a cation such as that already mentioned under A, and B represents a group which can be replaced by the nucleophilic radical of the compound of the formula V, in particular acyloxy having 1 to 4 C atoms, preferably acetoxy, halogen, preferably chlorine or bromine, and azido group, a carbamoyloxy group or a 2-mercaptopyridine N-oxide radical.

Suitable reactive derivatives of the carboxylic acids of the formula III are, in particular, the halides, preferably chlorides and bromides, and also the anhydrides and mixed anhydrides, the azides and activated esters, preferably esters of p-nitrophenol, 2,4-dinitrophenol, methylene cyanohydrin, N-hydroxysuccinimide and N-hydroxyphthalimide, and particularly preferably esters of 1-hydroxy-benztriazole and 6-chloro-1-H-hydroxybenztriazole. Suitable mixed anhydrides are, in particular, mixed anhydrides of lower alkanoic acids, for example acetic acid and, particularly preferably, substituted acetic acids, such as, for example, trichloroacetic acid, pivalic acid or cyanoacetic acid. Mixed anhydrides of carbonic acid half-esters, which are obtained, for example, by reacting the carboxylic acid of the formula III in which $R^1$ does not denote hydrogen, with benzyl, p-nitrobenzyl, isobutyl, ethyl or allyl chloroformate, are, however, also particularly suitable.

The activation can also be effected by reacting the carboxylic acids of the formula III with a product obtained from the reaction of, for example, phosgene, thionyl chloride, thionyl bromide, oxalyl chloride, phosphorus pentachloride or phosphorus oxychloride, with an N-dialkyl-substituted carboxylic acid amide, such as, for example, dimethylformamide, dimethylacetamide or N-methylpyrrolidone. The reaction product formed from dimethylformamide and one of the abovementioned halides is also described in the literature as the Vilsmeier reagent.

The activated derivatives can be reacted in the form of substances which have been isolated, or can also be reacted in situ. In general, the reaction of the cephem derivatives of the formula II with a carboxylic acid of the formula III or with an activated derivative of the latter is carried out in the presence of an inert solvent. Solvents which are particularly suitable are chlorinated hydrocarbons, such as, preferably, methylene chloride and chloroform; ethers, such as, for example, diethyl ether or diisopropyl ether and, preferably, tetrahydrofuran and dioxane; ketones, such as, preferably, acetone and butanone; amides, such as, preferably, dimethylformamide, dimethylacetamide or N-methylpyrrolidone, or water. It can also prove advantageous to use mixtures of the said solvents. This is often the case if the cephem compound of the formula II is reacted with an activated derivative of the carboxylic acid of the formula III, which has been formed in situ.

The reaction of cephem compounds of the formula II with carboxylic acids of the formula III or activated derivatives thereof can be carried out within a temperature range from about −50° to about +80° C., preferably between −20° and +50° C. and particularly preferably between −20° C. and room temperature.

The reaction time depends on the reactants, the temperature and the solvent or mixture of solvents, and is normally between about ¼ and about 72 hours.

In individual cases it can also prove advantageous to subject the free carboxylic acid of the formula III to direct reaction with a cephem compound of the formula II in which A' denotes, as a protective group, an ester radical which can easily be removed, such as, preferably, tert.-butyl or trimethylsilyl, in which case a dehydrating agent is added in an approximately equimolar amount, preferably in a slight excess. Examples of possible dehydrating agents are carbodiimides, in particular dicyclohexylcarbodiimides. This reaction is carried out in inert solvents, such as, preferably, methylene chloride, dimethylformamide, tetrahydrofuran, dioxane or mixtures thereof.

The reaction of activated derivatives of the carboxylic acids of the formula III with cephem compounds of the formula II is preferably carried out in an alkaline medium having a pH above 7, in particular at pH values between about 7 and about 9. This is effected by adding, to the reaction mixture, a base, such as, preferably, potassium carbonate, bicarbonate or hydroxide, sodium carbonate, bicarbonate or hydroxide, pyridine or a trialkylamine, such as, for example, triethylamine, N-methylmorpholine or ethyldiisopropylamine, or potassium tert.-butylate.

It can also be preferable to carry out the reaction by subjecting a 1-hydroxy-benztriazole or 6-chlorohydroxy-benztriazole ester of the carboxylic acids of the formula III to a direct reaction with cephem compounds of the formula II in a solvent, without adding an acid-binding agent. Solvents which have proved suitable are, in particular, open-chain and cyclic tertiary amides, particularly preferably dimethylformamide, dimethylacetamide and N-methylpyrrolidone.

The removal of $R^1$ can be effected by gentle methods which are generally customary in β-lactam and peptide chemistry, such as hydrolysis in acids, preferably formic acid or trifluoroacetic acid, or hydrogenolysis in the presence of noble metal catalysts. However, depending on the protective group, it is also possible to use special cleavage reagents, such as, for example, optionally substituted thioureas, for the removal of α-halogenoacyl groups.

The removal of the groups R'', $R^3$ and A', insofar as they have the function of a protective group, can also be effected by gentle hydrolytic or hydrogenolytic methods which are customary in β-lactam and peptide chemistry, in which connection special mention should be made of hydrolysis reactions carried out in inorganic and organic acids, such as, preferably, trifluoroacetic acid or dilute formic acid.

The reaction of compounds of the formula VI with compounds of the formula V is preferably carried out by reacting one equivalent of a compound of the formula VI with at least one equivalent of a compound of the formula V, in a solvent. An excess, up to about a 10-fold excess, of the compound of the formula V has an advantageous effect on the yield. It is preferable to use an excess of 1 to 200%. Examples of solvents which do not impede the reaction are water, acetone, butanone, chloroform, nitrobenzene, methylene chloride, ethylene chloride, dimethylformamide, dimethylacetamide, β-methylpyrrolidone, methanol, ethanol, ethyl acetate, butyl acetate, diethyl ether, diisopropyl ether, tetrahydrofuran and acetonitrile, preferably water.

Of these solvents, the hydrophilic solvents, preferably acetone, methanol, ethanol, dimethylformamide and acetonitrile, can also be used as a mixture with water. The reaction is carried out in a pH range from about 5 to about 8, preferably at a neutral pH.

The sodium or potassium salts of the compounds of the formula V can also be employed in the reaction.

The reaction temperature can be varied within a wide range. As a rule, the reaction is carried out at about 50° to about 80° C., preferably at about 65° C.

The abovementioned compounds of the formula V in which R denotes alkoxy, alkenoxy, alkinoxy, cycloalkoxy, aryloxy or aralkoxy, which can be substituted in the manner indicated above, can be prepared by reacting 2-mercapto-4-methyl-1,3-thiazoleacetic acid with an alcohol ROH in which R has the meaning indicated above, in a manner which is known from the literature, in the presence or absence of a solvent and in the presence of a catalyst, such as, for example, hydrochloric acid. It is also possible to react the thiazoleacetic acid with the alcohols in a manner which is known from the literature, by adding carbodiimides in an inert solvent. The compound of the formula V can also be synthesized by cyclization. In this case, the β-halogenolevulinic acid ester is first prepared, in a manner known from the literature, by esterifying the acid with an alcohol ROH in which R has the meaning indicated above. The β-halogenolevulinic acid ester can be converted into the thiazole by reaction with ammonium dithiocarbamate in an aqueous alcoholic solution, it being possible to vary the mixing ratio within wide limits, at 0° to 30° C., preferably at 5° to 10° C.

The abovementioned compounds of the formula V, in which R represents one of the optionally substituted amino groups mentioned, can be prepared, for example, by reacting a compound of the formula V, in which R can be an alkyl-O group having 1 to 4 C atoms, preferably methoxy and ethoxy, in an inert solvent, at elevated temperatures of about 40° to about 100° C., preferably 50° to 60° C., with an amine which can be substituted in the manner indicated.

In addition, compounds of the formula V in which R represents one of the optionally substituted amino groups indicated, can also be obtained by reacting β-halogenolevulinic acids, in which halogen can represent chlorine, bromine or iodine, with the amines, in the presence of a dehydrating agent, such as, for example, carbodiimides, preferably a dicyclohexylcarbodiimide, in an aprotic solvent and at an elevated temperature of about 30° to about 100° C., preferably 60° to 70° C., to give the β-halogenoamides.

The amides are then converted into the thiazole by reaction with ammonium dithiocarbamate in an aqueous alcoholic solution, it being possible to vary the mixing ratio within wide limits, at about 0° to 30° C., preferably at 5° to 10° C.

The starting compounds of the formulae III and VI are known from the literature or can be obtained by processes which are known from the literature.

Starting compounds of the formula II can be obtained by the same procedure as that described for the reaction of the compounds of the formula V with compounds of the formula VI. The compounds of the formula I which are obtained in accordance with the invention exhibit a remarkably good antibacterial activity against both Gram-positive and Gram-negative bacterial organisms.

The new compounds also have an unexpectedly good action against bacteria which form penicillinase and cephalosporinase. Since they exhibit, in addition, advantageous toxicological and pharmacological properties, they are valuable chemotherapeutic agents.

The invention also relates, therefore, to medicinal formulations for the treatment of microbial infections, which are characterized by containing one or more of the compounds according to the invention.

The products according to the invention can also be used in combination with other active compounds, for example compounds belonging to the series comprising the penicillins, cephalosporins or aminoglycosides.

The compounds of the formula I can be administered orally, intramuscularly or intravenously.

Medicinal preparations containing, as the active compound, one or more compounds of the formula I can be prepared by mixing the compounds of the formula I with one or more pharmacologically acceptable excipients or diluents, such as, for example, fillers, emulsifiers, lubricants, taste correctives, colorants or buffer substances, and bringing the mixture into a suitable pharmaceutical form of preparation, such as, for example, tablets, dragees or capsules, or a solution or suspension which is suitable for parenteral administration. Examples of excipients or diluents which may be mentioned are tragacanth, lactose, agar-agar, polyglycols, talc, ethanol and water. Suspensions or solutions in water are preferentially suitable for parenteral administration. It is also possible to administer the active compounds as such, in a suitable form, for example in capsules, without excipients or diluents.

Suitable doses of the compounds of the formula I are about 0.4 to 20 g/day, preferably 0.5 to 4 g/day, for an adult having a body weight of about 60 kg. Administration can be carried out in individual doses or, generally, in multiple doses, it being possible for an individual dose to contain an amount of about 50 to 1,000 mg, preferably 100 to 500 mg, of the active compound.

Compared with similar cephem derivatives which are known from Belgian Pat. No. 865,632, the compounds according to the invention are distinguished by unexpectedly superior antibacterial and pharmacokinetic properties.

In addition to the compounds mentioned in the illustrative embodiments, it is possible to prepare, in accordance with the invention, for example, the compounds I which are mentioned in the following tables:

TABLE 1

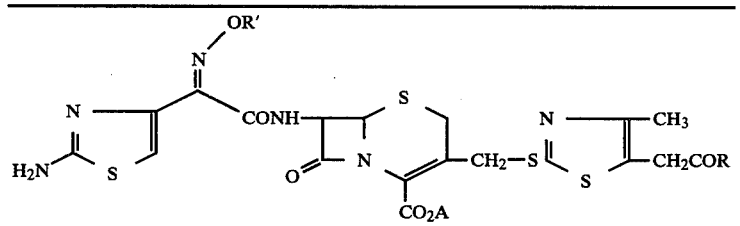

| R' | R |
|---|---|
| —CH$_3$ | —O—(CH$_2$)$_3$—CH$_3$ |
| —CH$_3$ | —O—CH=CH$_2$ |
| —CH$_3$ | —O—CH=CH—O—CH$_3$ |
| —CH$_3$ | —O—CH=CH—C$_6$H$_5$ |
| —CH$_3$ | —O—CH$_2$—O—CH$_3$ |
| —CH$_3$ | —O—C≡CH |
| —CH$_3$ | —O—C(=CH$_2$)—CH$_3$ |
| —CH$_3$ | —O—CH$_2$—CH$_2$—C≡CH |
| —CH$_3$ | —O—CH$_2$—CH$_2$Cl |
| —CH$_3$ | —O—CH$_2$—COOH |
| —CH$_3$ | —O—CH(cyclopropyl) |
| —CH$_3$ | —O—CH$_2$—C(=O)—NH$_2$ |

TABLE 2

| R' | R |
|---|---|
| —CH$_2$—COOH | —O—CH$_2$—CH$_3$ |
| —CH$_2$—COOH | —O—CH$_2$—CH$_2$—O—C$_6$H$_5$ |
| —CH$_2$—COOH | —O—CH$_2$—CH—(CH$_3$)$_2$ |
| —CH$_2$—COOH | —O—CH$_2$—CH=CH$_2$ |
| —CH$_2$—COOH | —O—CH$_2$—C≡CH |

TABLE 2-continued

| R' | R |
|---|---|
| —CH₂—COOH | —O—CH₂—C₆H₄—OCH₃ (p-methoxybenzyl ether) |
| —CH₂—COOH | —O—CH(CH₃)—C₆H₅ |
| —CH₂—COOH | —O—(CH₂)₃—CH₃ |
| —CH₂—COOH | —O—CH=CH—C₆H₅ |
| —CH₂—COOH | —O—CH=CH—O—C₆H₅ |
| —CH₂—COOH | —O—CH₂—O—CH₃ |
| —CH₂—COOH | —O—C≡CH |
| —CH₂—COOH | —O—C(=CH₂)—CH₃ |
| —CH₂—COOH | —O—CH₂—CH₂Cl |
| —CH₂—COOH | —O—CH₂—COOH |
| —CH₂—COOH | —O—CH₂—C(=O)—NH₂ |
| —CH₂—CH₂—COOH | —O—CH₂—CH₃ |
| —CH₂—CH₂—COOH | —O—CH₂—CH(CH₃)₂ |
| —CH₂—CH₂—COOH | —O—CH₂—CH=CH₂ |
| —CH₂—CH₂—COOH | —O—CH₂—C₆H₄—OCH₃ |
| —CH₂—CH₂—COOH | —O—CH(CH₃)—C₆H₅ |
| —CH₂—CH₂—COOH | —O—CH₂—O—CH₃ |
| —CH₂—CH₂—COOH | —O—CH=CH—C₆H₅ |
| —CH₂—CH₂—COOH | 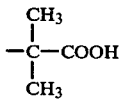 —O—CH(—CH₂—CH₂—) (epoxide) |

TABLE 3

| R' | R |
|---|---|
| —C(CH₃)₂—COOH | —O—CH₂—CH₃ |
| —C(CH₃)₂—COOH | —O—CH₂—CH(CH₃)₂ |
| —C(CH₃)₂—COOH | —O—CH₂—O—CH₃ |
| —C(CH₃)₂—COOH | —O—CH₂—CH=CH₂ |
| —C(CH₃)₂—COOH | —O—CH₂—C₆H₄—OCH₃ |
| —C(CH₃)₂—COOH | —O—CH(CH₃)—C₆H₅ |
| —C(CH₃)₂—COOH | —O—CH₂—C₆H₅ |
| —C(CH₃)₂—COOH | —O—CH=CH—C₆H₅ |
| —C(CH₃)₂—COOH | —O—CH(—CH₂—CH₂—) (epoxide) |

TABLE 4

| R' | R |
|---|---|
| —CH₂—C(=O)—NH₂ | —O—CH₂—CH₃ |
| —CH₂—C(=O)—NH₂ | —O—CH₂—CH(CH₃)₂ |
| —CH₂—C(=O)—NH₂ | —O—CH₂—O—CH₃ |
| —CH₂—C(=O)—NH₂ | —O—CH₂—CH=CH₂ |
| —CH₂—C(=O)—NH₂ | —O—CH₂—C₆H₄—OCH₃ |
| —CH₂—C(=O)—NH₂ | —O—CH(CH₃)—C₆H₅ |

TABLE 4-continued

| R' | R |
|---|---|
| —CH$_2$—C(=O)—NH$_2$ | —O—CH=CH—C$_6$H$_5$ |

The examples illustrate the invention, without limiting it thereto.

EXAMPLE 1

7-β-<α-syn-Methoximino-α-(2-aminothiazol-4-yl)-acetamido>-3-(4-methyl-5-p-methoxybenzyloxycarbonylmethyl-1,3-thiazol-2-ylthiomethyl)-3-cephem-4-carboxylic acid 760 mg of α-syn-methoximino-α-(2-aminothiazol-4-yl)-acetic acid were dissolved in 20 ml of dry dimethylacetamide, and 530 mg of hydroxy-benztriazole and 790 mg of dicyclohexylcarbodiimide were added. The yellow solution was stirred for 2 hours and the urea formed was filtered off with suction. A solution of 2 g of 7-amino-3-(4-methyl-5-p-methoxybenzyloxycarbonylmethyl-1,3-thiazol-2-ylthiomethyl)-3-cephem-4-carboxylic acid in 10 ml of dimethylacetamide was added to the solution remaining after filtration.

The mixture was stirred overnight at room temperature and water was added to it slowly. The precipitate was filtered off with suction and purified with water.

I.R.: 3318, 2940, 1780, 1730, 1675 cm$^{-1}$

NMR (DMSO) δ ppm: 2.13 s 3H, CH$_3$; 5.0 s 2H, 2CH$_2$, 5.63 m 1H 7H; 6.66 s 1H 5H syn; 7.0 m 4H aromatic; 9.43 d. 1H 7NH Preparation of 7-Amino-3-(4-methyl-5-p-methoxybenzyloxycarbonylmethyl-1,3-thiazol-2-ylthiomethyl)-3-cephem-4-carboxylic acid 20 ml of water and 10 ml of acetone were added to 2.72 g of 7-aminocephalosporanic acid. 1.68 g of sodium bicarbonate in 20 ml of water were added to the mixture, followed by 3.03 g of 2-mercapto-4-methyl-5-(p-methoxybenzyloxycarbonylmethyl)-1,3-thiazole. The pH was adjusted to 6.5 with 2N HCl and the mixture was heated at 65° C. After 6 hours and after the mixture had stood overnight, the acetone was evaporated on a rotary evaporator and the residue was extracted with ethyl acetate. The aqueous residue was acidified to pH 2.8 and the precipitate was filtered off with suction.

NMR (DMSO) β ppm: 2.33 s 3H CH$_3$ thiazole

EXAMPLE 2

7-β-<α-syn-Methoximino-α-(2-aminothiazol-4-yl)-acetamido>-3-(4-methylbenzyloxycarbonylmethyl-1,3-thiazol-2-ylthiomethyl)-3-cephem-4-carboxylic acid was prepared analogously to Example 1.

I.R.: 1773, 1735, 1632

NMR (DMSO) δ ppm: 5.1 s 2H CH$_2$; 5.53 q 1H 7H; 6.7 s 1H 5H; 7.3 s 5H aromatic.

EXAMPLE 3

7-β-<α-syn-Methoximino-α-(2-aminothiazol-4-yl)-acetamido>-3-(4-methyl-5-p-methoxybenzyloxycarbonylmethyl-1,3-thiazol-2-ylthiomethyl)-3-cephem-4-carboxylic acid.

9.5 g of the sodium salt of 7-β-<α-syn-methoximino-α-(2-aminothiazol-4-yl)-acetamido>-cephalosporanic acid were dissolved in 150 ml of water and the pH of the solution was adjusted to 7.2 with 3 ml of saturated sodium bicarbonate solution. 9.0 g of 2-mercapto-4-methyl-5-(p-methoxybenzyloxycarbonylmethyl)-1,3-thiazole, dissolved in 150 ml of acetone were then added.

The mixture was stirred at 65° for 12 hours. The pH was kept at 6.0 by adding sodium bicarbonate solution in stages. After cooling, the acetone was evaporated in vacuo and the residue was extracted several times with ethyl acetate. The aqueous phase was concentrated somewhat, in order to expel the ethyl acetate, and was then acidified to pH 2.8 with dilute hydrochloric acid, while being cooled thoroughly. The resulting precipitate was filtered off with suction and dried.

I.R.: 3318, 2940, 1780, 1730, 1675 cm$^{-1}$

NMR (DMSO) δ ppm: 2.13 s 3H CH$_3$; 5.0 s 2H CH$_2$; 5.63 q 1H 7H; 6.66 s 1H 5H syn; 7.0 m 4H aromatic; 9.43 d 1H 7NH

EXAMPLE 4

7-β-<-α-syn-Methoximino-α-(2-aminothiazol-4-yl)-acetamido>-3-(4-methyl-5-benzyloxycarbonylmethyl-1,3-thiazol-2-ylthiomethyl)-3-cephem-4-carboxylic acid was obtained by a procedure analogous to that described in Example 3.

I.R.: 3315, 2940, 1780, 1734, 1675 cm$^{-1}$

NMR (DMSO) δ ppm: 2.13 s 3H CH$_3$; 5.0 s 2H CH$_2$; 5.63 q 1H 7H; 6.66 s 1H 5H syn; 7.0 m 4H aromatic; 9.43 d 1H 7NH

EXAMPLE 5

7-β-<α-syn-Methoximino-α-(2-aminothiazol-4-yl)-acetamido>-3-[4-methyl-5-(3,4-dimethoxyphenoxycarbonylmethyl)-1,3-thiazol-2-ylthiomethyl]-3-cephem-4-carboxylic acid (Obtained analogously to Example 3).

I.R.: 1775, 1662, 1520 cm$^{-1}$

NMR (DMSO) δ ppm: 2.2 s 3H CH$_3$; 5.03 d. 1H; 3.7 s 6H OCH$_3$; 5.7 q 1H 7H 6.66 s 1H 5H syn; 6.86 s 2H aromatic; 9.5 d. 1H 7H

EXAMPLE 6

7-β-<α-syn-Methoximino-α-(2-aminothiazol-4-yl)-acetamido>-3-(4-methyl-5-p-chlorophenoxycarbonylmethyl-1,3-thiazol-2-ylthiomethyl)-3-cephem-4-carboxylic acid (Obtained analogously to Example 3).

I.R.: 1775 cm$^{-1}$, 1630 cm$^{-1}$

NMR (DMSO) δ ppm: 2.2 ppm s 3H thiazole CH$_3$; 3.83 CH$_2$ 3.1 s 2H CH$_2$; 5.7 q. 1H 7H; 6.73 s syn 5H thiazole; 7.36 s 3H aromatic; 9.56 d. 1H NH

EXAMPLE 7

7-β-<α-syn-Methoximino-α-(2-aminothiazol-4-yl)-acetamido>-3-(4-methyl-5-cinnamyloxycarbonylmethyl-1,3-thiazol-2-ylthiomethyl)-3-cephem-4-carboxylic acid (Obtained analogously to Example 3).

I.R.: 1775, 1726, 1670 cm$^{-1}$

NMR (DMSO) ppm: 2.33 s 3H CH$_3$; 3.8 s 2H CH$_2$; 4.73 d. 2H CH$_2$=; 5.1 d 1H 6H; 5.73 q. 1H 7H; 6.5 d 2H CH=CH; 6.7 s 1H 5H thiazole; 7.36 m 5H; 9.53 d. 1H 7NH

EXAMPLE 8

7-β-<α-syn-Methoximino-α-(2-aminothiazol-4-yl)-acetamido>-3-(4-methyl-5-p-methoxyphenoxycarbonylmethyl-1,3-thiazol-2-ylthiomethyl)-3-cephem-4-carboxylic acid (Obtained analogously to Example 3).

EXAMPLE 9

7-β-<α-syn-Methoximino-α-(2-aminothiazol-4-yl)-acetamido>-3-(4-methyl-5-β-phenylethoxycarbonylmethyl-1,3-thiazol-2-ylthiomethyl)-3-cephem-4-carboxylic acid (Obtained analogously to Example 3).
I.R.: 1770, 1640 cm$^{-1}$
NMR (DMSO) δ ppm: 2.2 ppm s 3H CH$_3$ thiazole; 3.8 s 4H CH$_2$; 5.1 d. 1H 6H; 5.7 q. 1H 7H; 6.7 s 1H 5H thiazole; 7.13 s 5H; 9.5 d. 1H NH

EXAMPLE 10

7-β-<α-syn-Methoximino-α-(2-aminothiazol-4-yl)-acetamido>-3-(4-methyl-5-α-phenylethoxycarbonylmethyl-1,3-thiazol-2-ylthiomethyl)-3-cephem-4-carboxylic acid (Obtained analogously to Example 3).
I.R.: 1773, 1630
NMR (DMSO) δ ppm: 2.23 s 3H CH$_3$ thiazole; 3.9 s 2H CH$_2$ 16.8 s 1H 5H; 7.3 s 5H aromatic; 9.5 d. 1H 7NH

EXAMPLE 11

7-β-<α-syn-Methoximino-α-(2-aminothiazol-4-yl)-acetamido>-3-(4-methyl-5-β-phenoxyethoxycarbonylmethyl-1,3-thiazol-2-ylthiomethyl)-3-cephem-4-carboxylic acid (Obtained analogously to Example 3).
NMR (DMSO) δ ppm; 2.23 s 3H CH$_3$ thiazole; 3.9 s 2H CH$_2$; 5.83 q. 1H 7H; 6.8 s 1H 5H; 7.3 s 5H m; 9.5 d. 1H 7NH

EXAMPLE 12

7-β-<α-syn-Methoximino-α-(2-aminothiazol-4-yl)-acetamido>-3-(4-methyl-5-isobutoxycarbonylmethyl-1,3-thiazol-2-yl-thiomethyl)-3-cephem-4-carboxylic acid (Obtained analogously to Example 3).
I.R.: 1780, 1725, 1672
NMR (DMSO) δppm: 0.8 s 3H; 0.9 s 3H CH$_3$; 2.2 s 3H CH$_3$; 3.86 s 2H CH$_2$; 5.06 d. 1H 6H; 5.7 q. 1H 7H; 6.66 s 1H thiazole 5H; 9.5 d. 7NH

EXAMPLE 13

7-β-<α-syn-Methoximino-α-(2-aminothiazol-4-yl)-acetamido>-3-(4-methyl-5-tert.-butoxycarbonylmethyl-1,3-thiazol-2-ylthiomethyl)-3-cephem-4-carboxylic acid (Obtained analogously to Example 3).
I.R.: 1760, 1638
NMR (DMSO) δppm: 1.4 s 9H—(CH$_3$)$_3$; 2.2 s 3H thiazole CH$_3$; 5.1 d 6H; 5.73 q. 1H; 6.7 s 1H, 5H; 9.5 d 1H NH

EXAMPLE 14

7-β-<α-syn-Methoximino-α-(2-aminothiazol-4-yl)-acetamido>-3-(4-methyl-5-allyloxycarbonylmethyl-1,3-thiazol-2-ylthiomethyl)-3-cephem-4-carboxylic acid (Obtained analogously to Example 3).
I.R.: 1770, 1730, 1660
NMR (DMSO) δppm: 2.2 s 3H CH$_3$ thiazole; 3.9 s 2H CH$_2$; 4.6 s 2H CH$_2$; 5.13

EXAMPLE 15

7-β-<α-syn-Methoximino-α-(2-aminothiazol-4-yl)-acetamido>-3-[4-methyl-5-(2-propinyloxycarbonylmethyl)-1,3-thiazol-2-ylthiomethyl]-3-cephem-4-carboxylic acid (Obtained analogously to Example 3).
I.R.: 1778, 1680 cm$^{-1}$
NMR (DMSO) δppm: 2.2 s 3H CH$_3$ thiazole; 3.8 s 2H CH$_2$; 4.7 d 2H CH$_2$; 5.02 d 1H 6H; 5.7 q. 1H 7H; 6.66 s 1H 5H thiazole; 9.49 d 1H 7NH

EXAMPLE 16

7-β-<α-syn-Methoximino-α-(2-aminothiazol-4-yl)-acetamido>-3-(4-methyl-5-carbamoylmethyl-1,3-thiazol-2-ylthiomethyl)-3-cephem-4-carboxylic acid (Obtained analogously to Example 3).
I.R.: 1770, 1670
NMR (DMSO) δppm: 2.2 s 3H CH$_3$ thiazole; 3.76 s 2H CH$_2$; 3.03 d 1H 6H; 5.66 q. 1H 7H; 6.66 s 1H 5H; 9.49 d. 1H NH

EXAMPLE 17

7-β-<α-syn-Methoximino-α-(2-aminothiazol-4-yl)-acetamido>-3-(4-methyl-5-N-phenylcarbamoylmethyl-1,3-thiazol-2-ylthiomethyl)-3-cephem-4-carboxylic acid (Obtained analogously to Example 3).
I.R.: 1775, 1640
NMR (DMSO) δppm: 2.26 s 3H CH$_3$; 5.03 d 1H 6H; 5.63 q. 1H 7H; 6.66 ppm s 1H thiazole; 7.33 m 4H aromatic; 9.5 d. 1H 7H

EXAMPLE 18

7-β<α-syn-Methoximino-α-(2-aminothiazol-4-yl)-acetamido<-3-(4-methyl-5-N-methylcarbamoylmethyl-1,3-thiazol-2-ylthiomethyl)-3-cephem-4-carboxylic acid (Obtained analogously to Example 3).

EXAMPLE 19

7-β-<α-syn-Methoximino-α-(2-aminothiazol-4-yl)-acetamido>-3-(4-methyl-5-β-methoxymethylcarbonylmethyl-1,3-thiazol-2-ylthiomethyl)-3-cephem-4-carboxylic acid (Obtained analogously to Example 3).
NMR (D$_2$O): 2.2 s 3H CH$_3$ thiazole, 3.3 s 3H OCH$_3$, 3.93 s 3H NOCH$_3$; 3.65 s 2H CH$_2$; 5.1 d 1H 6H; 5.7 d 1H 7H; 6.9 s 1H thiazole

EXAMPLE 20

7-β-<α-syn-Methoximino-α-(2-aminothiazol-4-yl)-acetamido>-3-(4-methyl-5-ethoxycarbonylmethyl-1,3-thiazol-2-ylthiomethyl)-3-cephem-4-carboxylic acid (Obtained analogously to Example 3).

I.R.: = 1774 cm$^{-1}$

= 1723 cm$^{-1}$

NMR (DMSO) δppm: 1.18 p . t 3H, 2.18 3H; 3.79 s; 4.07 q, 4.22 q, 5.05 d. 1H; 5.70 q 1H; 6.70 s 1H; 7,11 2H; 9.48 d. 1H

EXAMPLE 21

7-β-<α-syn-Methoximino-α-2-aminothiazol-4-yl)-acetamido>-3-(4-methyl-5-methoxycarbionylmethyl-1,3-thiazol-2-ylthiomethyl)-3-cephem-4-carboxylic acid (Obtained analogously to Example 3).

I.R.: 1775 cm$^{-1}$, 1730 cm$^{-1}$, 1680 cm$^{-1}$

NMR (DMSO) δppm: 2.23 s 3H; 3.64 s 3H; 3.80 s CH$_2$oxime; 3.9 s 2H; 4.25 q. CH$_2$; 5.08 d 6H; 5.73 dd 1H; 6.70 s 1H 7.13 s 9.53 d

|  | C | H | N | S |
|---|---|---|---|---|
| Analysis, calculated: | 41.0 | 3.9 | 13.6 | 20.8 |
| found: | 41.0 | 3.9 | 13.5 | 20.0 |

Preparation of starting compounds

EXAMPLE A

2-Mercapto-4-methyl-5-methoxycarbonyl-1,3-thiazole 12.0 g of α-(2-mercapto-4-methyl)-1,3-thiazoleacetic acid were dissolved in 100 ml of methanol, and 2.0 ml of concentrated hydrochloric acid were added. The mixture was stirred for 4 hours at room temperature. It was then concentrated in vacuo. Ethyl acetate was added to the residue and the mixture was washed several times with sodium bicarbonate solution. The combined ethyl acetate extracts were dried over MgSO$_4$ and were evaporated to dryness in vacuo.

I.R.: 1635, 1748 cm$^{-1}$

NMR (DMSO) δppm: 2.03 ppm s 3H, 3.26 s 2H: 3.6 s 3H

EXAMPLE B

2-Mercapto-4-methyl-5-(p-methoxybenzyloxycarbonylmethyl)-1,3-thiazole 10.8 g of α-(2-mercapto-4-methyl)-1,3-thiazoleacetic acid were dissolved in 100 ml of methylene chloride and 15 ml of dimethylformamide. After adding 570 mg of dimethylaminopyridine and 8.1 g of anisyl alcohol, the mixture was cooled with ice and 13.8 g of dicyclohexylcarbodiimide in 50 ml of methylene chloride were added dropwise. The mixture became slightly warm and was stirred at room temperature for 1.5 hours. The precipitated urea were filtered off with suction, the filtrate was evaporated under a good vacuum on a rotary evaporator and the residue was dissolved in ethyl acetate and washed with sodium bicarbonate solution. The ethyl acetate extract was dried with sodium sulfate and concentrated. The residue was triturated with ether and the product was recrystallized from methanol.

I.R.: 1748, 1630, 1620 cm$^{-1}$

NMR (DMSO) δppm=2.06 ppm s 3H thiazole CH$_3$,

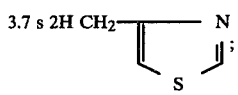

3.76 s 3H OCH$_3$; 5.03 s 2H CH$_2$—O; 6.75–7.33 m 4H aromatic H

Analysis, calculated: C 54.4 H 4.9 N 4.8 found: C 54.0 H 5.1 N 4.9

The following were prepared analogously to Example B:

(C)

2-Mercapto-4-methyl-5-(benzyloxycarbonylmethyl)-1,3-thiazole

NMR (DMSO) δppm=2.05 ppm s 3H thiazole CH$_3$;

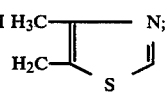

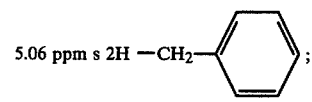

7.2 ppm s 5H aromatic

(D)

2-Mercapto-4-methyl-5-(3,4-dimethoxybenzyloxycarbonylmethyl)-1,3-thiazole

I.R.: 1730, 1637, 1603 cm$^{-1}$

NMR (DMSO): 2.03 ppm s 3H CH$_3$; 3.23 s 2H CH$_2$ δppm: 3.7 ppm s 6H OCH$_3$; 5.0 s 2H CH$_2$—O; 6.86 m 3H aromatic

(E)

2Mercapto-4-methyl-5-(p-chlorobenzyloxycarbonylmethyl)-1,3-thiazole

I.R.: 1730, 1630 cm$^{-1}$

(F)

2-Mercapto-4-methyl-5-(cinnamyloxycarbonylmethyl)-1,3-thiazole

I.R.: 1726, 1625 cm$^{-1}$

NMR (DMSO) δppm: 2.06 ppm s 3H CH$_3$; 3.7 ppm s 2H CH$_2$; 4.7 ppm d 2H=CH$_2$; 6.43 ppm q 1H CH=7.33 ppm m 5H

(G)

2-Mercapto-4-methyl-5-(p-methoxyphenoxycarbonyl)-1,3-thiazole

NMR (DMSO) δppm: 6.9 m 4H aromatic

(H)

2-Mercapto-4-methyl-5-(α-phenylethoxycarbonylmethyl)-1,3-thiazole

NMR (DMSO) δppm: 2.03 s 3H thiazole; 1.4 s 3H CH$_3$; 3.7 s 2H CH$_2$;

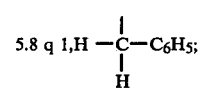

7.3 m aromatic H

(I)

2-Mercapto-4-methyl-5-(β-phenylethoxycarbonylmethyl)-1,3-thiazole

NMR (DMSO) δppm: 2.0 s 3H thiazole; 3.6 2H CH$_2$; 4.26 triplet CH$_2$; 7.16 m 5H aromatic

(J)
2-Mercapto-4-methyl-5-(α-phenoxyethoxycarbonylmethyl)-1,3-thiazole

(K)
2-Mercapto-4-methyl-5-(isobutoxycarbonylmethyl)-1,3-thiazole

NMR (DMSO) δppm:

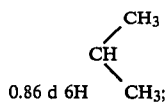

0.86 d 6H 2.06 s 3H thiazole CH₃, 2.76 ppm d 2H CH₂, 3.8 d 2H CH₂

(L)
2-Mercapto-4-methyl-5-(tert.-butoxycarbonylmethyl)-1,3-thiazole

NMR (DMSO) δppm: 1.4 s 9H 3 CH₃; 2.1 3H CH₃; 3.93 2H CH₂

(M)
2-Mercapto-4-methyl-5-(allyloxycarbonylmethyl)-1,3-thiazole

NMR (DMSO) δppm: 2.03 s 3H thiazole CH₃; 3.63 s 2H CH₂; 4.53 d 2H CH₂; 5.23 m CH; CH₂=; 5.87 m; 1H CH=

(N)
2-Mercapto-4-methyl-5-(2-propinyloxycarbonylmethyl)-1,3-thiazole

NMR (DMSO) δppm: 2.03 s 3H CH₃ thiazole; 2.56 1H q. 3.7 s 2H CH₂; 4.7 d 2H

(O)
2-Mercapto-4-methyl-5-(β-methoxyethoxycarbonylmethyl)-1,3-thiazole

I.R.: cm⁻¹ 3593, 2940, 2720, 1740, 1650, 1630, 1470, 1450

NMR (DMSO ) δppm: 2.1 s 3H CH₃; 3.25 s 3H OCH₃; 3.4–3.4 s 2H; 4.3; 7.95

(P)
2-Mercapto-4-methyl-5-(carbamoylmethyl)-1,3-thiazole 40 ml of water were added to 20.0 g of methyl α-(2-mercapto-4-methyl-1,3-thiazoleacetate in an autoclave and 100 ml of liquid ammonia were added, while cooling. The mixture was shaken in the autoclave at room temperature for 22 hours under nitrogen. Expelling the ammonia by blowing with nitrogen left a yellow substance. Water was added to this substance and the pH was adjusted to 1 with dilute hydrochloric acid. The precipitate was filtered off with suction, washed with water and dried.

I.R.: 1650–80, 1595 cm⁻¹

NMR (DMSO) δppm: 2.03 s 3H; 3.3 s 2H

Analysis: calculated: 38.4% C 4.2% H 15.0% N 34.1% S C₆H₈N₂S₂O found: 37.7% C 4.1% H 14.5% N 35.0% S

(Q)
2-Mercapto-4-methyl-5-(N-methylcarbamoylmethyl)-1,3-thiazole

NMR (DMSO) δppm: 3.36 s 3H NH CH₃; 7.86 calculated s NH; 2.06 s 3H; 2.72 s 2H

(R)
2-Mercapto-4-methyl-5-(N-phenylcarbamoylmethyl)-1,3-thiazole 18.0 g of β-bromolevulinic acid anilide were dissolved in 50.0 ml of methanol, and 8.0 g of freshly prepared ammonium dithiocarbamate, dissolved in 10 ml of water, were added dropwise at 0°. The temperature rose frm 0° to 10° C. Stirring was continued for one day at room temperature, the ammonium bromide was filtered off with suction and the filtrate was concentrated on a rotary evaporator. The residue was recrystallized from a mixture of methanol and water.

I.R.: 3270, 3024, 2862, 1656, 1600, 1528 cm⁻¹

NMR (DMSO) δppm: 2.2 s 3H CH₃ thiazole; 3.62 s CH₂ 2H; 7.4 m 5H aromatic

Preparation of β-bromolevulinic acid anilide 5.0 g of aniline, 9.5 g of β-bromolevulinic acid and 10.0 g of dicyclohexylcarbodiimide were each dissolved in 25 ml portions of tetrahydrofuran. The solution of the carbodiimide was added dropwise to the solution of aniline and of β-bromolevulinic acid, while cooling at 0°. The precipitate was formed immediately. The dicyclohexylurea was filtered off with suction after 24 hours and the filtrate was concentrated in a rotary evaporator. The oil which remained was dissolved in ethyl acetate and washed with sodium bicarbonate solution and dilute hydrochloric acid. Drying the solution and evaporating the solvent left a pale brown oil.

I.R.: 3230, 2935, 2845, 1710, 1600 cm⁻¹

NMR (DMSO) δppm: 2.33 d 3H CH₃; 3.0 q 2H CH₂; 4.86 q 1H CH; 7.3 m 5H aromatic.

We claim:

1. A cephem compound of the formula

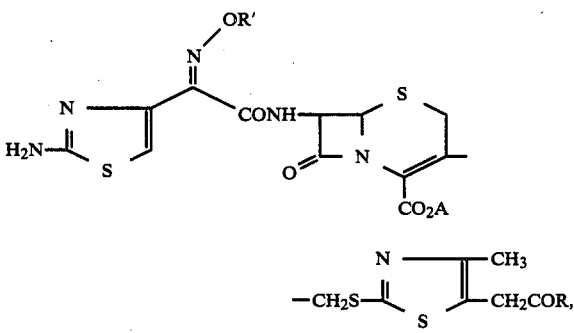

wherein
R is C₁-C₆-alkoxy or C₁-C₆-alkoxy substituted by hydroxyl, halogen, carboxyl, aminocarbonyl, C₁-C₄-alkoxy, C₁-C₄-alkoxy-C₁-C₄-alkoxy, C₁-C₄-alkoxy-C₁-C₄-alkoxy-C₁-C₄-alkoxy, phenyl, phenoxy, or phenyl or phenoxy mono- or poly-substituted by hydroxyl, C₁-C₄-alkoxy, halogen, carboxyl, C₁-C₄-alkoxycarbonyl, or aminocarbonyl, or wherein R is C₂-C₆-alkenoxy, C₂-C₆-alkinoxy, C₃-C₆-cycloalkoxy, or C₂-C₆-alkenoxy substituted by phenyl or by phenyl mono- or polysubstituted by hydroxyl, C₁-C₄-alkyl, C₁-C₄-alkoxy, halogen, carboxyl, C₁-C₄-alkoxycarbonyl or aminocarbonyl, or wherein R is phenoxy or phenoxy mono- or polysubstituted by halogen, C₁-C₄-alkyl, hydroxyl, C₁-C₄-alkoxy, nitro, amino, C₁-C₄-alkylamino, di-C₁-C₄- alkylamino, sulfo, aminocarbonyl, carboxyl, or $C_1$–$C_4$-alkoxycarbonyl, or wherein R is phenyl-$C_1$–$C_6$-alkoxy wherein phenyl is mono- or poly-substituted by amino, $C_1$–$C_4$-alkylamino, di-$C_1$–$C_4$-alkylamino, or sulfo, R' is $C_1$–$C_4$-alkyl, alkyl substituted by halogen, hydroxyl, or sulfo or wherein R' is carboxymethyl wherein the carboxyl group may be present in the form of a physiologically acceptable salt or ester, or wherein R' is $C_1$–$C_4$-alkoxycarbonylmethyl, aminocarbonylmethyl, or cyanomethyl wherein methylene may be mono- or di-substituted by $C_1$–$C_4$-alkyl and wherein two alkyl substituents may also be linked to form a 3-membered to 6-membered carbocyclic ring;

the group R'O— is in the syn position; and

A is hydrogen or a physiologically acceptable cation.

2. A compound as in claim 1 which is 7-β-[α-syn-methoximino-α-(2-aminothiazol-4-yl)acetamido]-3-(4-methyl-5-p-methoxybenzyloxycarbonylmethyl-1,3-thiazol-2-ylthiomethyl)-3-cephem-4-carboxylic acid.

3. A compound as in claim 1 which is 7-β-[α-syn-methoximino-α-(2-aminothiazol-4-yl)acetamido]-3-(4-methyl-5-benzyloxycarbonylmethyl-1,3-thiazol-2 ylthiomethyl)-3-cephem-4-carboxylic acid.

4. A compound as in claim 1 which is 7-β-[α-syn-methoximino-α-(2-aminothiazol-4-yl)acetamido]-3-(4-methyl-5-p-chlorophenoxycarbonylmethyl-1,3-thiazol-2-ylthiomethyl)-3-cephem-4-carboxylic acid.

5. A compound as in claim 1 which is 7-β-[α-syn-methoximino-α-(2-aminothiazol-4-yl)acetamido]-3-(4-methyl-5-isobutoxycarbonylmethyl-1,3-thiazol-2-ylthiomethyl)-3-cephem-4-carboxylic acid.

6. A compound as in claim 1 which is 7-β-[α-syn-methoximino-α-(2-aminothiazol-4-yl)acetamido]-3(4-methyl-5-tert.butoxycarbonylmethyl-1,3-thiazol-2ylthiomethyl)-3-cephem-4-carboxylic acid.

7. A pharmaceutically formulation comprising an anti-bacterially effective amount of a compound as in claim 1 and a pharmaceutically acceptable carrier thereof.

8. The method of treating a bacterial infection in a patient which comprises administering to said patient an anti-bacterially effective amount of a compound as in claim 1.

* * * * *